(12) United States Patent
Wade et al.

(10) Patent No.: US 7,199,157 B2
(45) Date of Patent: Apr. 3, 2007

(54) USE OF TREPROSTINIL TO IMPROVE KIDNEY FUNCTIONS

(75) Inventors: Michael Wade, Chapel Hill, NC (US); Roger Andrew Jeffs, Chapel Hill, NC (US); Kathryn Bronstein, Jupiter, FL (US); Deborah Strootman, Tucson, AZ (US)

(73) Assignee: United Therapeutics Corporation, Silver Spring, MD (US)

( * ) Notice: Subject to any disclaimer, the term of this patent is extended or adjusted under 35 U.S.C. 154(b) by 42 days.

(21) Appl. No.: 11/012,722

(22) Filed: Dec. 16, 2004

(65) Prior Publication Data
US 2005/0165110 A1    Jul. 28, 2005

Related U.S. Application Data

(60) Provisional application No. 60/529,621, filed on Dec. 16, 2003.

(51) Int. Cl.
*A61K 31/19* (2006.01)
(52) U.S. Cl. .................................... 514/571
(58) Field of Classification Search ..................... None
See application file for complete search history.

(56) References Cited

U.S. PATENT DOCUMENTS

| | | | |
|---|---|---|---|
| 4,306,075 | A | 12/1981 | Aristoff |
| 5,153,222 | A | 10/1992 | Tadepalli et al. |
| 6,054,486 | A | 4/2000 | Crow et al. |
| 6,441,245 | B1 | 8/2002 | Moriarty et al. |
| 6,521,212 | B1 | 2/2003 | Cloutier et al. |
| 6,528,688 | B2 | 3/2003 | Moriarty et al. |
| 2005/0080140 | A1* | 4/2005 | Hatae et al. ............... 514/573 |
| 2005/0085540 | A1* | 4/2005 | Phares et al. ............... 514/530 |
| 2005/0165111 | A1* | 7/2005 | Wade et al. ............... 514/573 |
| 2005/0282901 | A1* | 12/2005 | Phares et al. ............... 514/571 |

OTHER PUBLICATIONS

Clapp, L. H., et al., "Differential Effects of Stable Prostacyclin Analogs on Smooth Muscle Proliferation and Cyclic AMP Generation in Human Pulmonary Artery", Am. J. Respir. Cell Mol. Biol., vol. 26, pp. 194-201 (2002).
Medline Plus® Medical Encyclopedia: Diabetic nephropathy, pp. 1-4, www.nlm.nih.gov/medlineplus/ency/article/000494.htm, date unavailable.
Medline Plus® Medical Encyclopedia: Immune response, pp. 1-3, www.nlm.nih.gov/medlineplus/ency/article/000821.htm, date unavailable.
Medline Plus® Medical Encyclopedia: Mesangial proliferative glomerulonephritis, pp. 1-3, www.nlm.nih.gov/medlineplus/ency/article/000487.htm, date unavailable.
Patterson, J. H., et al., "Acute Hemodynamic Effects of the Prostacyclin Analog 15AU81 in Severe Congestive Heart Failure", The Amer. J. Card., vol. 75, pp. 26A-33A (1995).
Raychaudhuri, B., et al., "The Prostacyclin Analogue Treprostinil Blocks NFχB Nuclear Translocation in Human Alveolar Macrophages", J. Biol. Chem., vol. 277, No. 36, pp. 33344-33348 (2002).
Shionoya, S., "Diagnostic criteria of Buerger's disease", Intl. J. Cardio. 66 (Suppl. 1), pp. S243-245 (1998).
Tyle, P., "Iontophoretic Devices for Drug Delivery", Pharma. Res., vol. 3, No. 6, pp. 318-326 (1986).
van Dijk, C., et al., "Pathogenesis of Diabetic Nephropathy", Rev. in Endocrine & Metabolic Disorders, vol. 5, No. 3, pp. 237-248 (2004).

* cited by examiner

*Primary Examiner*—Raymond J Henley, III
(74) *Attorney, Agent, or Firm*—Foley & Lardner LLP

(57) ABSTRACT

The present invention describes novel methods for using Treprostinil or its derivative, or a pharmaceutically acceptable salt thereof, for improving kidney functions, such as urine output, and treating symptoms associated with kidney malfunction or failure. The invention also relates to kits for the improvement of kidney functions and the treatment of symptoms associated with kidney malfunction or failure, comprising an effective amount of Treprostinil or its derivative, or a pharmaceutically acceptable salt thereof.

13 Claims, No Drawings

USE OF TREPROSTINIL TO IMPROVE KIDNEY FUNCTIONS

FIELD OF INVENTION

The invention relates to the use of Treprostinil or its derivative, or a pharmaceutically acceptable salt thereof, to improve functions of the kidney, such as urine production, and to treat symptoms associated with kidney malfunction or failure. This invention also relates to kits to be used for this purpose.

BACKGROUND

Treprostinil, also known as UT-15, is a known compound disclosed in U.S. Pat. No. 4,306,075 in example 33. Treprostinil is a synthetic analog of epoprostenol, a prostaglandin $F_1$. The activities ascribed to the various compounds of this patent include inhibition of smooth muscle cell proliferation, inhibition of platelet aggregation, inhibition of cytokine secretion, reduction of gastric secretion, vasodialation and bronchodilation.

U.S. Pat. No. 5,153,222 discloses the use of Treprostinil and related compounds to treat pulmonary hypertension. U.S. Pat. No. 6,054,486 discloses the use of Treprostinil and related compounds to treat peripheral vascular disease, such as peripheral arterial occlusive disease and intermittent claudication. Patterson et al., *Amer. J of Cardiology*, 75: 26A–33A (1995), have shown vasodilator effects of Treprostinil in patients with class III or class IV heart failure.

Clapp et al., *Am. J. Respir. Cell. Mol. Biol.*, 26(2): 194–201 (2002), have shown that Treprostinil inhibits proliferation of human pulmonary arterial smooth muscle cells. Raychaudhuri et al,. *J. Biol. Chem.*, 277(36): 33344–8 (2002), have disclosed that Treprostinil inhibits inflammatory cytokine (tumor necrosis factor-α, interleukin-1β, interleukin-6, and granulocyte macrophage colony-stimulating factor) secretion and gene expression by human alveolar macrophages.

Healthy kidney functions includes producing urine, maintaining water balance by removing excess fluid from the body, removing waste products (e.g., urea and creatinine) from the blood, maintaining normal blood chemistry (e.g., proper concentrations of sodium, potassium, chloride, calcium, magnesium, sulfate, phosphate and hydrogen in extracellular fluid), and producing hormones, such as renin (helps regulate blood pressure), erythropoietin (helps maintain proper blood volume by stimulating the production of red blood cells) and calcitriol (helps facilitate calcium absorption from food).

Mesangial proliferative glomerulonephritis is a uncommon kidney disorder characterized by swelling of the body (edema) and blood in the urine. It is caused by inflammation of an internal kidney structure (glomerulus), involving an increase in number of certain cells of the glomerular capillaries, known as mesangial cells. The mechanism that triggers the disorder is unknown, but it is believed to be some type of immune response (see e.g., www.nlm.nih.gov/medlineplus/ency/article/000821.htm), because inflammation of the glomeruli is associated with deposits of antibodies. During this kidney malfunction, the mesangial cells increase in size and number, which give the glomeruli a lumpy appearance (see e.g., www.nlm.nih.gov/medlineplus/ency/article/000487.htm).

Diabetic nephropathy is the most common cause of renal failure in the United States and other developed countries. Mesangial expansion contributes to glomerular basement membrane thickening in diabetic nephropathy leading to glomerulosclerosis. The mechanism contributing to these physiologic changes are directly related to the hyperglycemia and micorvascular dysfunction. Van Dijk, C. & Berl, T., 2004 "Pathogenesis of Diabetic Nephropathy. Reviews in Endocrine and Metabolic Disorders; 5: 237–248. See e.g., www.nlm.nih.gov/medlineplus/ency/article/000494.htm.

SUMMARY

Administration of Treprostinil or its derivative, or a pharmaceutically acceptable salt thereof, improves kidney functions and alleviates symptoms associated with kidney malfunction or failure. Treprostinil is well suited for such use because the compound is a stable analogue of prostaglandin, can be used in intravenous administration, is not degraded when it passes through the lungs, and has a long biological half-life.

Accordingly, present invention provides for the improvement of kidney functions and/or the treatment of symptom associated with kidney malfunction or failure in a mammal, comprising administering to a mammal in need thereof an effective amount of Treprostinil or its derivative, or a pharmaceutically acceptable salt thereof. The present invention also provides for kits for accomplishing this purpose.

DETAILED DESCRIPTION

The inventors believe that therapies that enhance blood flow to the kidneys are effective therapies for improving kidney functions in subjects with malfunctioning or failing kidneys and for treating symptoms or disorders associated with that malfunction or failure. The inventors also believe that therapies that inhibit inappropriate proliferation of mesangial cells can induce improved kidney functions in subjects with kidney disorders such as mesangial proliferative glomerulonephritis or diabetic nephropathy.

Prostacyclins are small molecules that have been previously shown to cause dilation of large blood vessels, relaxation of smooth muscle, inhibition of smooth muscle proliferation, as well as inhibition of platelet aggregation. Similar actions by Treprostinil on microvascular and capillaries in the kidney are believed to help enhance blood flow to the kidneys, which improves kidney functions. Inventors also believe that actions by Treprostinil reduce or inhibit the inappropriate proliferation of mesangial cells seen in kidney disorders, such as mesangial proliferative glomerulonephritis. While additional modes of action may exist, administration of Treprostinil to subjects improves kidney functions, and/or treat of symptom associated with kidney malfunction or failure, by either enhancing renal blood flow or having of an anti-proliferation effect on mesangial cells, or by both actions.

The present invention relates to methods for improving kidney functions or treating symptoms associated with kidney malfunction or failure in mammals, comprising administering to a subject, preferably a human being, in need thereof an effective amount of Treprostinil and/or a derivative thereof and/or a pharmaceutically acceptable salt thereof. Suitable derivatives include acid derivatives, prodrugs, sustained release forms, inhaled forms, oral forms, a polymorph and an isomer of Treprostinil, including those disclosed in U.S. Pat. No. 6,521,212 and co-pending Ser. No. 60/472,407.

The invention includes a method for improving at least one kidney function in a subject with a disease or condition that causes kidney malfunction or failure, comprising administering to a subject in need thereof an effective amount of Treprostinil or its derivative, or a pharmaceutically acceptable salt thereof. In one embodiment, the kidney function comprises urine production, removal of excess body fluid, removal of waste products from the blood, maintenance of normal blood chemistry or hormone production. In another embodiment, the disease or condition that causes kidney malfunction or failure comprises an increase in proliferation of mesangial cells. In another embodiment, the disease or condition that causes kidney malfunction or failure comprises mesangial proliferative glomerulonephritis. The invention also may comprise a method for reducing or inhibiting the proliferation of mesangial cells in a subject with a disease or condition that causes kidney malfunction or failure.

The present invention also relates to kits for accomplishing such kidney improvement or symptom treatment comprising (i) an effective amount of Treprostinil or its derivative, or a pharmaceutically acceptable salt thereof, (ii) one or more pharmaceutically acceptable carriers and/or additives, and (iii) instructions for use in improving kidney functions or treating symptoms associated with kidney malfunction or failure.

The invention includes a kit for improving at least one kidney function in a subject with a disease or condition that causes kidney malfunction or failure, comprising (i) an effective amount Treprostinil or its derivative, or a pharmaceutically acceptable salt thereof, (ii) one or more pharmaceutically acceptable carriers and/or additives, and (iii) instructions for improving at least one kidney function. In one embodiment, the kidney function comprises urine production, removal of excess body fluid, removal of waste products from the blood, maintenance of normal blood chemistry or hormone production. In another embodiment, the disease or condition that causes kidney malfunction or failure comprises an increase in proliferation of mesangial cells. In another embodiment, the disease or condition that causes kidney malfunction or failure comprises mesangial proliferative glomerulonephritis.

Unless otherwise specified, the term "a" or "an" used herein shall mean "one or more."

As used herein, the phrase "instructions for use" shall mean any FDA-mandated labeling, instructions, or package inserts that relate to the administration of Treprostinil or its derivative, or a pharmaceutically acceptable salt thereof, for the purpose of improving kidney functions or treating symptoms associated with kidney malfunction or failure. For example, instructions for use may include, but are not limited to, indications for kidney malfunction or failure, indications for specific symptoms associated with reduced kidney functions, such as abnormally low urination, increased blood levels of creatinine and urea nitrogen, protein leakage in urine and/or pain, that can be ameliorated by Treprostinil, and recommended dosage amounts for subjects suffering from kidney malfunctions.

The term "acid derivative" is used herein to describe C1–4 alkyl esters and amides, including amides wherein the nitrogen is optionally substituted by one or two C1–4 alkyl groups.

The invention also includes bioprecursors or "pro-drugs" of Treprostinil, that is, compounds which are converted in vivo to Treprostinil or its pharmaceutically active derivatives thereof.

Further aspects of the present invention are concerned with the use of Treprostinil or its derivatives, or pharmaceutically acceptable salts thereof, in the manufacture of a medicament for improving kidney functions or treating symptoms associated with kidney malfunction or failure in mammals.

The present invention encompasses methods of using Treprostinil or its derivative, or a pharmaceutically acceptable salt thereof. In one embodiment, a method uses Treprostinil sodium, currently marketed under the trade name of REMODULIN®. The FDA has approved Treprostinil sodium for the treatment pulmonary arterial hypertension by injection of dose concentrations of 1.0 mg/mL, 2.5 mg/mL, 5.0 mg/mL and 10.0 mg/mL. The chemical structure formula for Treprostinil sodium is:

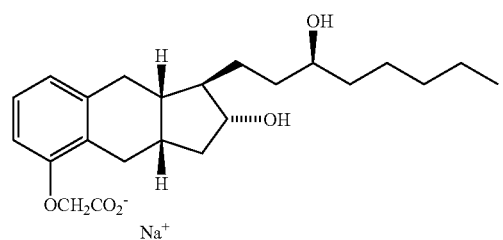

Treprostinil sodium is sometimes designated by the chemical names: (a) [(1R,2R,3aS,9aS)-2,3,3a,4,9,9a-hexahydro-2-hydroxy-1-[(3S)-3-hydroxyoctyl]-1H-benz[f]inden-5-yl]oxy]acetic acid; or (b) 9-deoxy-2',9-α-methano-3-oxa-4,5,6-trinor-3,7-(1',3'-interphenylene)-13,14-dihydro-prostaglandin $F_1$. Treprostinil sodium is also known as: UT-15; LRX-15; 15AU81; UNIPROST™; BW A15AU; and U-62,840. The molecular weight of Treprostinil sodium is 390.52, and its empirical formula is $C_{23}H_{34}O_5$.

The present invention extends to methods of using physiologically acceptable salts of Treprostinil, as well as non-physiologically acceptable salts of Treprostinil that may be used in the preparation of the pharmacologically active compounds of the invention.

Physiologically acceptable salts of Treprostinil include salts derived from bases. Base salts include ammonium salts (such as quaternary ammonium salts), alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of Treprostinil or its derivative, or a pharmaceutically acceptable salt thereof, which is required in a medication or diagnostic aid according to the invention to achieve the desired effect will depend on a number of factors, such as the specific application, the nature of the particular compound used, the mode of administration, the concentration of the compound used, and the weight and condition of the patient. A daily dose per patient for improving kidney functions and/or treating symptoms associated with kidney malfunction or failure may be in the range 25 µg to 250 mg; 0.5 µg to 2.5 mg, or 7 µg to 285 µg, per day per kilogram bodyweight. For example, an intravenous dose in the range 0.5 µg to 1.5 mg per kilogram bodyweight per day may conveniently be administered as an infusion of from 0.5 ng to 1.0 μg per kilogram bodyweight per minute. One possible dosage is 2.5 ng/kg/min, increased over 12 weeks by an amount of 2.50 ng/kg/min each week, until a target dose, such as 15 ng/kg/min, is reached. Infusion fluids suitable for this purpose contain, for example, from 10 ng to 1 μg per milliliter. Ampoules for injection contain, for example, from 0.1 μg to 1.0 mg and orally administrable unit dose formulations, such as tablets or capsules, contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from Treprostinil.

In the manufacture of a medicament or diagnostic aid according to the invention, hereinafter referred to as a "formulation," Treprostinil and/or its derivatives, and/or pharmaceutically acceptable salts thereof, may be admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.05% to 95% by weight of the active compound. One or more of Treprostinil or its derivatives, or pharmaceutically acceptable salts thereof, may be incorporated in the formulations of the invention, which may be prepared by any of the well known techniques of pharmacy for admixing the components.

In addition to Treprostinil, other pharmacologically active substances may be present in the formulations of the present invention which are known to be useful for improving kidney functions or treating symptoms associated with kidney malfunction or failure in mammals.

The formulations of the invention include those suitable for parenteral (e.g., subcutaneous, intramuscular, intradermal, or intravenous), oral, inhalation (in solid and liquid forms), rectal, topical, buccal (e.g., sub-lingual) and transdermal administration, although the most suitable route in any given case may depend on the nature and severity of the condition being treated and on the nature of the particular form of Treprostinil, as well as the physiologically acceptable salt or derivative thereof, which is being used.

Formulations of the present invention suitable for parenteral administration conveniently comprise sterile aqueous preparations of Treprostinil or its derivative, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations according to the invention may contain from 0.1 to 5% w/v of active compound and may be administered at a rate of 0.1 ml/min/kg. Alternatively, the invention may administered at a rate of 0.625 to 50 ng/kg/min. Alternatively, the invention may be administered at a rate of 10 to 15 ng/kg/min.

Formulations suitable for oral administration may be presented in discrete units, such as capsules, cachets, lozenges, or tablets, each containing a predetermined amount of Treprostinil or a physiologically acceptable salt or derivative thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising Treprostinil, or a physiologically acceptable salt or derivative thereof, in a flavored base, usually sucrose and acacia or tragacanth; and pastilles comprising the compound in an inert base such as gelatin and glycerin or sucrose and acacia.

Formulations suitable for rectal administration are preferably presented as unit dose suppositories. These may be prepared by admixing Treprostinil or its derivative, or a pharmaceutically acceptable salt thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w. Formulations for transdermal administration may be delivered by iontophoresis (see, for example, *Pharmaceutical Research,* 3(6): 318 (1986)) and typically take the form of an optionally buffered aqueous solution of Treprostinil or of a salt or derivative thereof. Suitable formulations comprise citrate or bis/tris buffer (pH 6) or ethanol/water and contain from 0.1 to 0.2M active ingredient.

The compounds of the present invention are conveniently prepared by methods the same as or analogous to those described in U.S. Pat. No. 4,306,075, U.S. Pat. No. 6,528,688 and U.S. Pat. No. 6,441,245.

Additional embodiments are within the scope of the invention. For example, in one embodiment, a method for improving at least one kidney function in a subject (such as a human being) with a disease or condition that causes kidney malfunction or failure comprises administering to a subject in need thereof an effective amount of Treprostinil or its derivative, or a pharmaceutically acceptable salt thereof.

In another embodiment, a kit for improving at least one kidney function in a subject (such as a human being) with a disease or condition that causes kidney malfunction or failure comprises (i) an effective amount of Treprostinil or its derivative, or a pharmaceutically acceptable salt thereof, (ii) one or more pharmaceutically acceptable carriers and/or additives, and (iii) instructions for improving at least one kidney function.

In certain embodiments, the kidney function is chosen from urine production, removal of excess body fluid, removal of waste products from the blood, maintenance of normal blood chemistry, hormone production or a combination thereof. In other embodiments, the disease or condition that causes kidney malfunction or failure comprises an increase in proliferation of mesangial cells. In another embodiment, the method further comprises reducing or inhibiting proliferation of mesangial cells in the subject with a disease or condition that causes kidney malfunction or failure.

In certain method embodiments, the Treprostinil or its derivative, or a pharmaceutically acceptable salt thereof, is administered subcutaneously, by continuous subcutaneous infusion, intravenously, in an orally available form selected from the group consisting of tablets and capsules, and/or by inhalation. In other embodiments, the effective amount of Treprostinil or its derivative, or a pharmaceutically acceptable salt thereof, is at least 1.0 ng/kg of body weight/min.

In certain kit embodiments, the Treprostinil or its derivative, or a pharmaceutically acceptable salt thereof, is in a form suitable for subcutaneous administration, continuous subcutaneous infusion, intravenously administration or inhalation. In other kit embodiments, the Treprostinil or its derivative, or a pharmaceutically acceptable salt thereof, is in an orally available form selected from the group consisting of tablets and capsules. In another kit embodiment, the effective amount of Treprostinil or its derivative, or a pharmaceutically acceptable salt thereof, is at least 1.0 ng/kg of body weight/min.

EXAMPLE

Administration of Treprostinil to Humans Suffering From Kidney Malfunction/Failure Patients suffering from poor kidney function are administered Treprostinil at a dosage starting at 0.625 to 1.25 ng/kg/min, which is progressively increased over time until a target dose is reached or until the dosage not tolerated by the patient. The target dose is determined by titration in patients for a clinical effect. The medication is delivered by a small pump that is connected to a catheter placed under the skin. In this manner, increasing dosages of Treprostinil are administered to patients by chronic continuous subcutaneous infusion. Common side effects at peak dose are expected and included headache and nausea. An example of one target dose is 10 ng/kg/min.

In one study, at least two patients suffering from poor kidney function, who were also on dialysis, exhibited improved urine production upon treatment with Treprostinil over the course of several weeks.

Patients receiving Treprostinil treatment experience improved kidney functions, such as urine production. The administration of Treprostinil improves kidney functions in patients suffering from kidney malfunction or failure, or exhibiting symptoms associated with kidney disorders such as mesangial proliferative glomerulonephritis or diabetic nephropathy.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method for improving at least one kidney function in a subject with a disease or condition that causes kidney malfunction or failure, comprising administering to a subject in need thereof an effective amount of Treprostinil or its derivative, or a pharmaceutically acceptable salt thereof, wherein said derivative is an acid derivative of Treprostinil, a pro-drug of Treprostinil, a sustained release form of Treprostinil, an inhaled. form of Treprostinil, an oral form of Treprostinil, a polymorph of Treprostinil or an isomer of Treprostinil.

2. The method of claim 1, wherein the kidney function is chosen from urine production, removal of excess body fluid, removal of waste products from the blood, maintenance of normal blood chemistry, hormone production or a combination thereof.

3. The method of claim 1, wherein the kidney function comprises urine production.

4. The method of claim 1, wherein the disease or condition that causes kidney malfunction or failure comprises an increase in proliferation of mesangial cells.

5. The method of claim 1, further comprising a reduction or inhibition of proliferation of mesangial cells in the subject with a disease or condition that causes kidney malfunction or failure.

6. The method of claim 1, wherein a pharmaceutically acceptable salt of Treprostinil is administered.

7. The method of claim 1, wherein the subject is a human being.

8. The method of claim 1, wherein the Treprostinil or its derivative, or a pharmaceutically acceptable salt thereof, is administered subcutaneously.

9. The method of claim 1, wherein the Treprostinil or its derivative, or a pharmaceutically acceptable salt thereof, is administered by continuous subcutaneous infusion.

10. The method of claim 1, wherein the Treprostinil or its derivative, or a pharmaceutically acceptable salt thereof, is administered intravenously.

11. The method of claim 1, wherein the Treprostinil or its derivative, or a pharmaceutically acceptable salt thereof, is administered in an orally available form selected from the group consisting of tablets and capsules.

12. The method of claim 1, wherein the Treprostinil or its derivative, or a pharmaceutically acceptable salt thereof, is administered by inhalation.

13. The method of claim 1, wherein the effective amount is at least 1.0 ng/kg of body weight/min.

* * * * *